United States Patent [19]

Clausen et al.

[11] Patent Number: 4,797,130
[45] Date of Patent: Jan. 10, 1989

[54] OXIDATIVE HAIR DYE COMPOSITION BASED ON 4-AMINO-2-AMINOMETHYL-PHENOLS

[75] Inventors: Thomas Clausen, Alsbach; Eugen Konrad, Darmstadt, both of Fed. Rep. of Germany

[73] Assignee: Wella Aktiengesellschaft, Darmstadt, Fed. Rep. of Germany

[21] Appl. No.: 93,744

[22] PCT Filed: Nov. 22, 1986

[86] PCT No.: PCT/EP86/00674
§ 371 Date: Jul. 27, 1987
§ 102(e) Date: Jul. 27, 1987

[87] PCT Pub. No.: WO87/03474
PCT Pub. Date: Jun. 18, 1987

[30] Foreign Application Priority Data

Dec. 7, 1985 [DE] Fed. Rep. of Germany ....... 3543345

[51] Int. Cl.$^4$ .................... A61K 7/13; C07C 10/344; C07C 91/44; C07D 263/22
[52] U.S. Cl. ......................... 8/421; 8/409; 8/416; 564/389; 564/390
[58] Field of Search ............ 8/421, 409, 416; 564/389, 390; 548/23

[56] References Cited

U.S. PATENT DOCUMENTS 2,843,585 7/1958 Surrey .................. 544/97
3,406,024 10/1968 Richter et al. ........... 71/98
3,622,629 11/1971 Lugosy .................. 564/330
3,762,922 10/1973 Lugosy et al. ............ 96/56

FOREIGN PATENT DOCUMENTS 0172139 2/1986 European Pat. Off.
0182187 5/1986 European Pat. Off.
2018836 10/1979 United Kingdom.

OTHER PUBLICATIONS

Chemical Extracts, vol. 101, 1984 (p. 534).
Chem. Abstracts, Div. 6, vol. 674, p. 1365, 9-1953 #103,533.

Primary Examiner—Paul Lieberman
Assistant Examiner—Ronald A. Krasnow
Attorney, Agent, or Firm—Michael J. Striker

[57] ABSTRACT

Oxidative hair dye composition based on 4-amino-2-aminomethyl-phenols of the general formula (I)

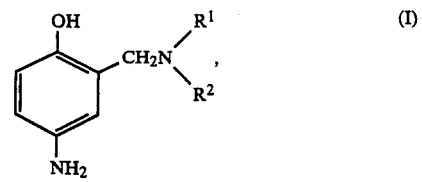

or its salts as developer substances, wherein $R^1$ and $R^2$ represent independently of one another hydrogen, alkyl, hydroxyalkyl, aminoalkyl, mono- or dialkylaminoalkyl, acylaminoalkyl, aryl- or alkylsulfonylaminoalkyl, carbamindoalkyl, acyl, aryl - or alkylsulfonyl or carbomoyl—wherein the alkyl radical has 1 to 4 carbon atoms in each case—or a heterocyclic, non-aromatic five- or six-membered ring is formed by means of $R^1$ and $R^2$ which can have an oxo group in addition.

The subject matter of the application is also the new developer substances of the general formula (XII)

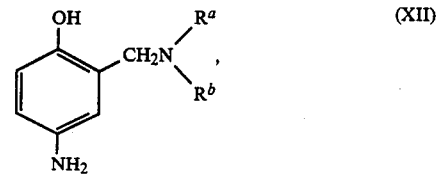

wherein $R^a$ equals hydrogen, alkyl, hydroxyalkyl, aminoalky, mono- or dialkylaminoalky, acylaminoalkyl, aryl- or alkylsulfonylaminoalkyl, carbamoyl, carbamido-alkyl, acyl, aryl- or alkylsulfonyl—wherein the alkyl radicals have 1 to 4 carbon atoms in each instance—and $R^b$ equals aminoalkyl, mono- or dialkylaminoalkyl, acylaminoalkyl, aryl- or alkylsulfonylaminoalkyl, carboamoyl, carbamidoalkyl, acyl, aryl- or alkylsulfonyl—wherein the alkyl radicals have 1 to 4 carbon atoms in each instance.

The developer substances of the formula (I), while having equally good dyeing behavior, have properties which are better physiologically than the p-aminophenol chiefly used previously for colorings in the red area.

12 Claims, No Drawings

OXIDATIVE HAIR DYE COMPOSITION BASED ON 4-AMINO-2-AMINOMETHYL-PHENOLS

DESCRIPTION

The subject matter of the invention is a composition for the oxidative coloring of hair based on 4-amino-2-amino-methyl-phenols as developer substances, as well as new 4-amino-2-aminomethyl-phenols.

In the area of hair coloring, oxidative dyestuffs have achieved considerable importance. The coloring is brought about by means of the reaction of certain developer substances with certain coupler substances in the presence of a suitable oxidizing agent.

2,5-diamino-toluene, 2,5-diamino-benzyl alcohol, p-aminophenol and 1,4-diamino-benzene particularly are used as developer substances. Resorcinol, 4-chlororesorcinol, 1-naphthol, m-aminophenol and derivatives of m-phenylene-diamine are among those coupler substances whose use is preferred.

Numerous special requirements are set for oxidative dyestuffs which are used for coloring human hair. For example, they must be harmless in toxicological and dermatological respects and must enable the desired intensity of coloring. In addition, a favorable light fastness, fastness to permanent waving and acids and rubbing fastness are required of the hair colorings which are achieved. But, in every instance, such hair colorings must remain stable over a period of at least 4 to 6 weeks without being influenced by light, rubbing or chemical agents. Moreover, it is necessary that a wide assortment of various color shades can be made by means of combining suitable developer and coupler substances. In order to achieve natural and especially fashionable shades in the red area, p-aminophenol is chiefly used, by itself or in a mixture with other developer substances, in combination with suitable coupler substances.

The developer p-aminophenol, chiefly used for the red area of the color scale until now, has recently been criticized with respect to physiological compatibility, while developer substances such as pyrimidine derivatives, which have been recommended more recently, are not completely satisfactory with respect to coloring.

Therefore, the problem arises of discovering an oxidative hair coloring composition based on developer substances for the red area which can better meet the aforementioned requirements.

It has now been found that the proposed problem is solved in an outstanding manner by means of a composition for the oxidative dyeing of hair based on a combination of developer substances and coupler substances, characterized in that it contains a 4-amino-2-aminophenol of the general formula (I)

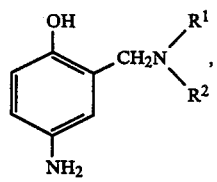

or its salt, as developer substance, wherein $R^1$ and $R^2$ designate independently of one another hydrogen, alkyl, hydroxyalkyl, aminoalkyl, mono- or dialkylamino-alkyl, acylaminoalkyl, aryl- or alkylsulfonylaminoalkyl, carbamido-alkyl, alkylsulfonyl—wherein the alkyl radical has 1 to 4 carbon atoms in each instance—arylsulfonyl, acyl or carbamoyl, or $R^1$ and $R^2$ form a heterocyclic, nonaromatic five-membered or six-membered ring, which can have an oxo group in addition.

The developer substances, according to the invention, of which the 4-amino-2-aminomethyl-phenol, the 4-amino-2-[(2'-hydroxyethyl)-aminomethyl]-phenol and the 4-amino-2-dimethylaminomethyl-phenol are preferred, are to be contained in the hair dye composition in a concentration of approximately 0.01 to 3.0 percent by weight, preferably 0.1 to 2.5 percent by weight.

Although the advantageous characteristics of the developer substances described here suggest the use of the latter as the only developers, it is, of course, also possible to use these developer substances of formula (I) together with known developer substances, such as 1,4-diamino-benzene, 2,5-diamino-toluene, 2,5-diamino-benzyl alcohol or 2,5-diamino-phenylethyl alcohol.

Of the known coupler substances, resorcinol, 4-chlororesorcinol, 4,6-dichlororesorcinol, 2-methyl-resorcinol, 2-amino-4-[(2'-hydroxyethyl)-amino]-anisol, 2,4-diamino-benzyl alcohol, 2,4-diamino-phenylethyl alcohol, m-phenylenediamine, 5-amino-2-methyl-phenol, 2,4-diamino-phenoxyethanol, 4-amino-2-hydroxy-phenoxyethanol, 1-naphthol, m-aminophenol, 3-amino-2-methyl-phenol, m-toluylenediamine, 4-hydroxy-1,2-methylene-dioxy-benzene, 4-amino-1,2-methylenedioxy-benzene, 4-[(2'-hydroxyethyl)-amino]-1,2-mehylenedioxy-benzene, 2,4-diamino-anisol, 2,4-diamino-phenetole, 4-hydroxy-indole, 3-amino-5-hydroxy-2,6-dimethoxy-pyridine and 3,5-diamino-2,6-dimethoxy-pyridine are chiefly taken into consideration as component part of the hair dye composition described here.

The aforementioned coupler and developer substances can be contained in the hair dye composition individually or in a mixture with one another.

The total quantity of the developer-coupler combination contained in the hair dye compositions described here should amount to approximately 0.1 to 5.0 percent by weight, preferably 0.5 to 4.0 percent by weight.

The developer substances are generally used in approximately equimolar quantities with respect to the coupler substances. However, it is not disadvantageous if the developer substance, in this respect, is present to a certain extent in greater or lesser quantities.

In addition, the hair dye composition of this application can contain other coloring components, for example, 6-amino-2-methyl-phenol and 2-amino-5-methyl-phenol, as well as other conventional direct-dyeing dyestuffs, for example, triphenylmethane dyestuffs, such as Diamond Fuchsine (C.I. 42 510) and Leather Ruby HF (C.I. 42 520), aromatic nitro dyestuffs, such as 2-nitro-1,4-diamino-benzene, 2-amino-4-nitro-phenol, 2-amino-5-nitro-phenol, 2-amino-4,6-dinitro-phenol, 2-amino-5-[(2'-hydroxyethyl)-amino]-nitrobenzene and 2-methylamino-5-[bis-(2'-hydroxyethyl)-amino]-nitrobenzene, azo dyestuffs such as Acid Brown 4 (C.I. 14 805) and dispersed dyestuffs such as 1,4-diamino-anthraquinone and 1,4,5,8-tetraamino-anthraquinone. The hair dye composition can contain these coloring components in quantities of approximately 0.1 to 4.0 percent by weight.

Of course, the coupler and developer substances, as well as the other coloring components, insofar as they are bases, can also be used in the form of physiologically compatible acid addition salts such as hydrochloride or sulfate, or—insofar as they have aromatic OH groups—in the form of salts with bases, for example, as alkali phenolates.

Moreover, other conventional cosmetic ingredients can also be present in the hair dye composition, for example, antioxidants, preferably ascorbic acid, thiogylcolic acid or sodium sulfite, perfume oils, complexing agents, wetting agents, emulsifying agents, thickeners, hair care materials, etc.

The preparation form can be a solution, for example, particularly an aqueous or aqueous-alcoholic solution. However, cream, gel or an emulsion are particularly preferred as preparation forms.

Its composition is a mixture of dyestuff components with the usual ingredients for such preparations.

The usual ingredients in solutions, creams, emulsions or gels are, for example, solvents such as water, lower aliphatic alcohols, for example, ethanol, propanol and isopropanol, as well as polyhydric alcohols such as ethylene glycol, glycerine and 1,2-propylene glycol, wetting agents or emulsifying agents from the classes of anionic, cationic, amphoteric or nonionogenic surface-active substances such as fatty alcohol sulfates, fatty alcohol ether sulfates, oxethylated fatty alcohol sulfates, alkyl sulfonates, alkylbenzene sulfonates, alkyltrimethyl-ammonium salts, alkyl-betaines, oxethylated fatty alcohols, oxethylated alkylphenols, fatty acid alkanol amides or oxethylated fatty acid esters; also thickeners such as higher fatty alcohols, bentonite, starch, cellulose derivatives such as carboxymethyl cellulose, alginates, vaseline, paraffin oil and fatty acids, as well as hair care materials such as cationic resins, lanolin derivatives, cholesterin, pantothenic acid and betaine. The aforementioned components are used in the amounts which are conventional for such purposes, for example, the wetting agents and emulsifying agents are used in concentrations of approximately 0.5 to 30 percent by weight, the thickeners are used in quantities of approximately 0.1 to 25 percent by weight and the hair care materials are used in a concentration of approximately 0.1 to 5.0 percent by weight.

According to the composition, the hair dye composition, according to the invention, can react in a slightly acidic, neutral or alkaline manner. In particular, they have a pH value in the alkaline area between 8.0 and 11.5, wherein they are preferably adjusted with ammonia. However, organic amines, for example, monoethanolamine and triethanolamine, or inorganic bases such as sodium hydroxide and potassium hydroxide, can also be used.

For application for the purpose of oxidative dyeing of hair, the aforementioned hair dye composition is mixed immediately prior to use with an oxidizing agent and a quantity of this mixture sufficient for the hair dyeing treatment, generally, approximately 60 to 200 g, according to the fullness of the hair, is applied to the hair.

Hydrogen peroxide or its addition compounds in urea, melamine or sodium borate in the form of a 3 to 12 percent, preferably a 6 percent, aqueous solution, chiefly come under consideration as oxidizing agents for the development of the hair coloring. If a 6 percent hydrogen peroxide solution is used as oxidizing agent, then the weight ratio between the hair dye composition and the oxidizing agent is 5:1 to 1:2, but preferably 1:1. Larger quantities of oxidizing agent are used in the hair dye composition chiefly in higher dyestuff concentrations or when a more intensive bleaching of the hair is intended. The mixture is allowed to act on the hair at 15° to 50° C. for approximately 10 to 45 minutes, preferably 30 minutes, the hair is then rinsed with water and dried. The hair is washed with a shampoo after this rinse, if necessary, and possibly rerinsed with a weak organic acid such as citric acid or tartaric acid. The hair is then dried.

The compounds of formula (I) can be produced by the three methods A, B and C described in the following.

A. By means of electrophilic substitution of p-nitrophenol (II) with various electrophiles according to diagrams 1, 2 or 3, possibly further reaction in the side chain, and the following reduction:

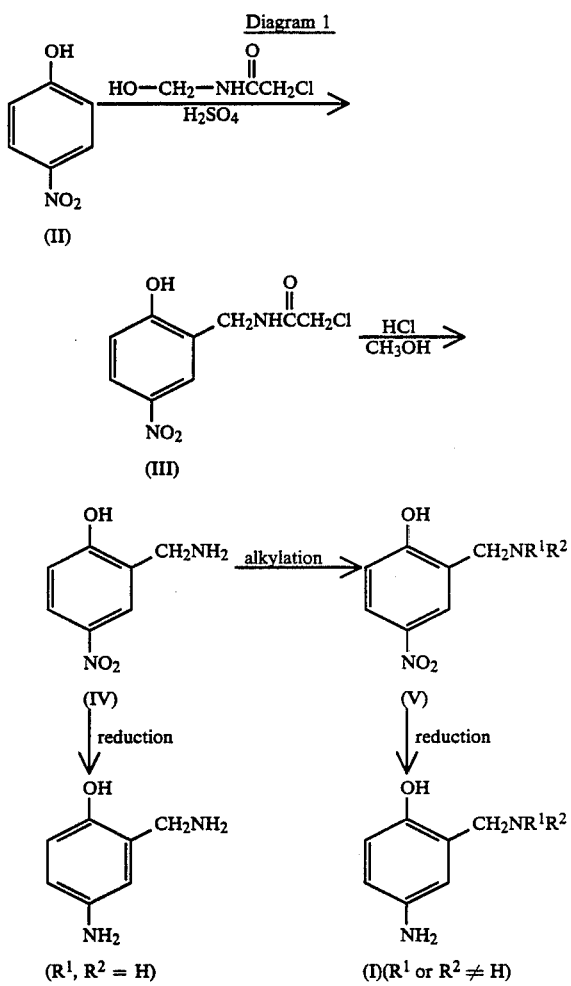

The production of the compound (III) is described in the literature on the subject (H. E. Zaugg, Synthesis 1984, pages 85 to 96) or can be effected in a manner analogous to G. E. Stokker et al., J. Med. Chem. 23, pages 1414 to 1427 (1980) and the DE-PS 21 63 908.

The compound (IV) (obtained by means of separating the amide (III)) serves as the starting material for an entire assortment of aminomethylphenols substituted in the side chain, but can also be converted into a developer substance of formula (I) directly by means of reduction.

The reduction of (IV) or (V) can be carried out catalytically, for example (with the use of a platinum catalyst, for example), wherein hydrazine can also be used as a hydrogen carrier in an advantageous manner.

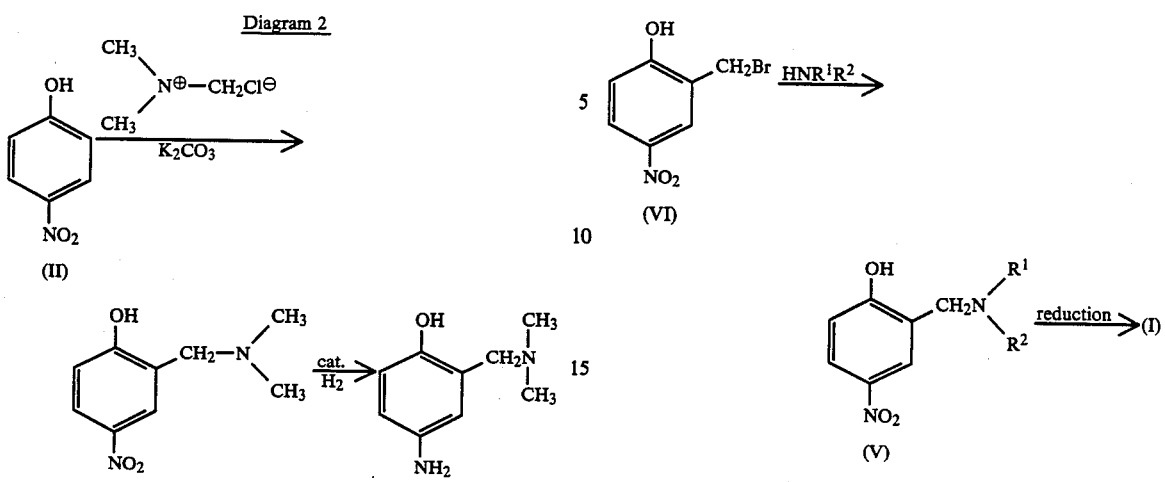

The reaction of the nitrophenol (II) can also be effected in a manner analogous to R. Ungaro et al., Synthesis 1983, pages 906 and 907, with N-methyl-N-methylene-methane-immoniumchloride. After the reduction, the dimethyl compound ($R^1$, $R^2$=$CH_3$) is obtained directly.

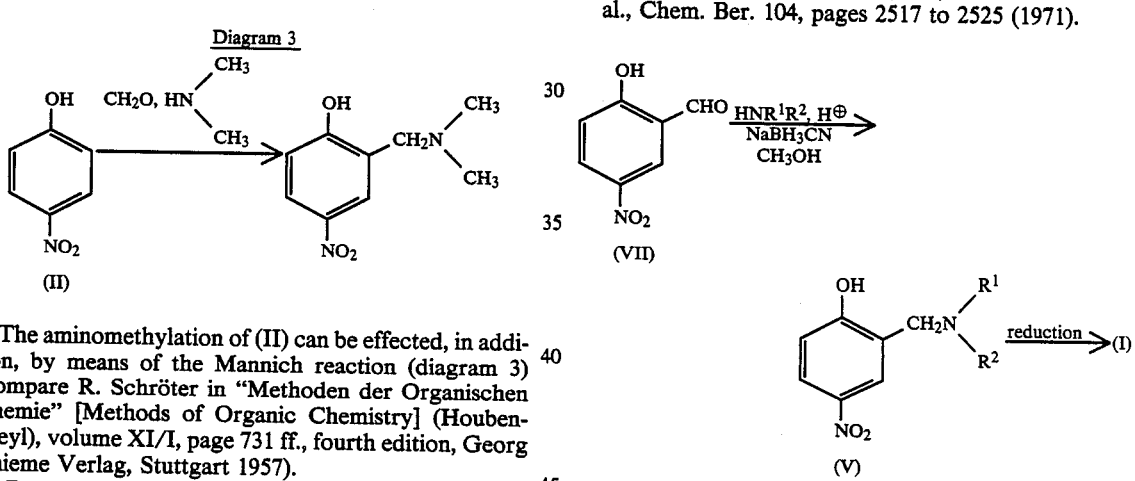

The aminomethylation of (II) can be effected, in addition, by means of the Mannich reaction (diagram 3) (compare R. Schröter in "Methoden der Organischen Chemie" [Methods of Organic Chemistry] (Houben-Weyl), volume XI/I, page 731 ff., fourth edition, Georg Thieme Verlag, Stuttgart 1957).

B. By means of substituting bromine in 2-hydroxy-5-nitro-benzylbromide (VI) an entire assortment of preliminary steps (V) can be produced with suitable amines. The reduction yields the developer substance of formula (I).

C. Finally, the developer substances, according to the invention, can be made advantageously by means of the reaction of the 4-nitro-salicylaldehyde (VII) with suitable amines and reduction of the resulting Schiff's bases or immonium compounds, for example, according to the method of R. F. Borch et al., J. Am. Chem. Soc. 93, pages 2897 to 2904 (1971) or F. Dallacker et al., Chem. Ber. 104, pages 2517 to 2525 (1971).

Another way of synthesizing is by way of oxazolidinone (VIII). This can be reduced directly to a developer substance of formula (I) on the one hand, but, on the other hand, it can also be used to produce additional compounds, according to the invention, according to the following diagram:

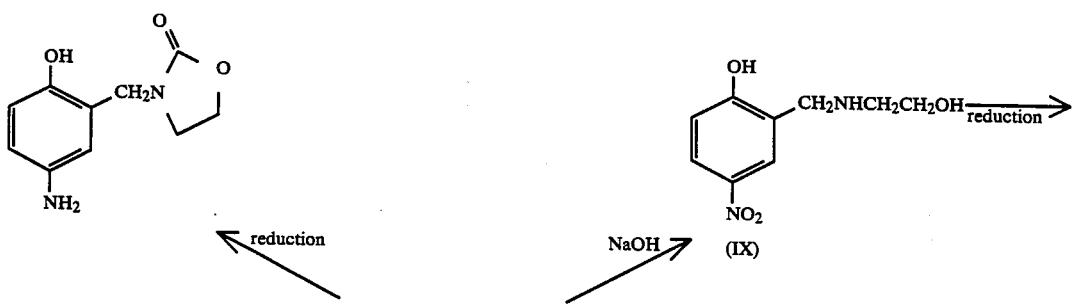

-continued

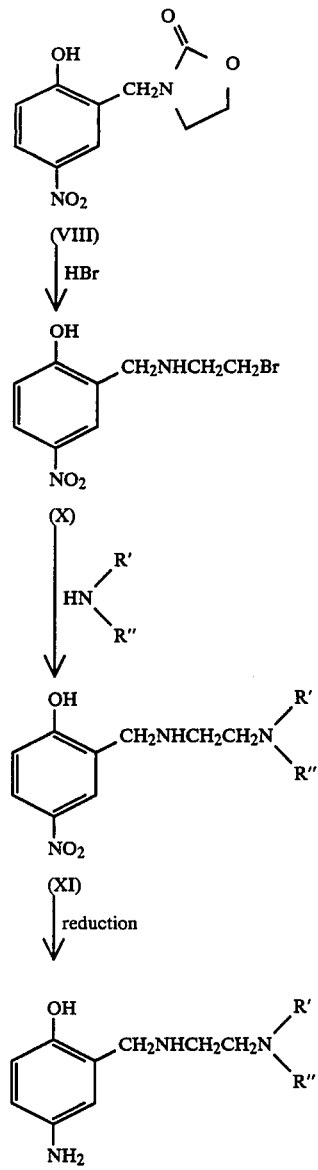

Numerous compounds of the formula (I) are already known. Its production is described in the following texts, among others:

Beilsteins Handbuch der Organischen Chemie [Beilsten's Handbook of Organic Chemistry] (1930) 13, 598; ibid (1973) 13, E III 1548; ibid (1985) 13, E IV 1691–1692;

Angelo et al., J. Med. Chem. (1983) 26, 1258–1267 and 1311–1316;

Burckhalter et al., J. Am. Chem. Soc. (1948), 70, 1363–1373.

The developer substances of the formula (I) are new in part. The subject matter of the present invention is therefore also new 4-amino-2-aminomethyl-phenols of the formula (XII)

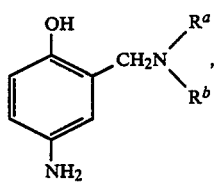

wherein $R^a$ equals hydrogen, alkyl, hydroxyalkyl, amino-alkyl, mono- or dialkylaminoalkyl, acylaminoalkyl, aryl- or alkylsulfonylaminoalkyl, carbamoyl, carbamidoalkyl, acyl, aryl- or alkylsulfonyl—wherein the alkyl radicals have 1 to 4 carbon atoms in each instance—$R^b$ equals aminoalkyl, mono- or dialkylaminoalkyl, acylaminoalkyl, aryl- or alkylsulfonyl-aminoalkyl, carbamoyl, carbamidoalkyl, acyl, aryl- or alkylsulfonyl—wherein the alkyl radicals have 1 to 4 carbon atoms in each instance.

Examples for compounds of formula (XII), according to the invention, are 2-acetamidomethyl-4-aminophenol and N-(5'-amino-2'-hydroxy-benzyl)-N',N'-diethyl-ethylenediamine.

The production of these new compounds is effected according to the production processes A, B and C, which were already described, and is explained in more detail in the production examples.

The salts of the compounds of formula (I) are obtainable by means of reaction with organic or inorganic acids or bases.

The developer substance of formula (I) and either as free base or in the form of its physiologically compatible salts with inorganic or organic acids, for example, as chloride, sulfate, phosphate, acetate, propionate, lactate or citrate, are to be used in the hair dye compositions, according to the invention. In the strongly alkaline medium, they can be present, in addition, as phenolate. The compounds of formula (I) are favorably soluble in water. Moreover, they have an excellent shelf stability, particularly as a component of the hair dye composition described here.

The hair dye composition, according to the invention, based on 4-amino-2-aminomethyl-phenols as developer substances, result in hair colorings with excellent fastness characteristics, particularly with respect to light fastness, washing fastness and rubbing fastness, and can be removed again with reducing agents.

In comparison to known developer substances currently in use for achieving red tints, the progress made in toxicological and dermatological respects by the use of the 4-amino-2-aminomethyl-phenols in the hair dye composition according to the present application is also of particular significance.

With respect to dyeing possibilities, the hair dye composition, according to the invention, offers a wide assortment of various shades of color which range from blond, brown, purple and violet to blue and black color tints, according to the type and composition of the dye components. The color tints are distinguished by their favorable dye intensities.

The very good dyeing properties of the hair dye composition according to the present application become apparent also in that this composition enables a dyeing of gray hair, which is not chemically damaged beforehand, easily and with good covering power.

In the following examples the subject matter of the invention is explained in more detail without being limited to these examples.

PRODUCTION EXAMPLES

Example 1

2-acetamidomethyl-4-amino-phenol (Method A)

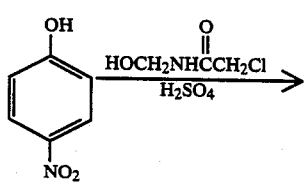

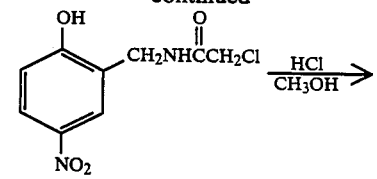

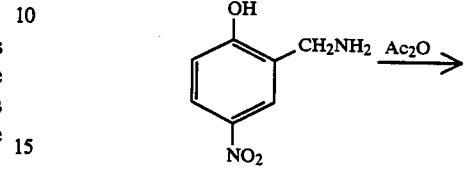

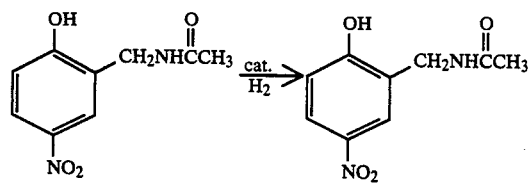

Step 1

2-chloroacetamidomethyl-4-nitro-phenol 13.9 g (0.1 mole) 4-nitro-phenol and 12.35 g (0.13 mole) N-hydroxymethyl-chloroacetamide (produced in a manner analogous to the instruction of J. D. Milkowski, D. F. Veber and R. Hirschmann, Org. Synth. 59, pages 190 to 195 (1979)) are finely ground together in a mortar and added by small amounts to 100 ml concentrated sulfuric acid, accompanied by stirring. The temperature increases to 53° C. It is stirred over night at room temperature and the reaction preparation is then poured on ice. The precipitate is separated using suction. The residue can be used in step 2 without further purification.

The dried compound melts at over 230° C. accompanied by decomposition.

Yield: 22 g (89.9 percent of theoretical)

Step 2

2-aminomethyl-4-nitro-phenol 12.2 g (0.056 mole) of chloroacetamido compound of step 1 is heated in 100 ml ethanol and 30 ml concentrated hydrochloric acid for 4 hours accompanied by refluxing. After dilution with water, it is neutralized with sodium bicarbonate and the precipitate is separated by suction, accompanied by rewashing with water. The residue is purified by means of reprecipitation. 3 g of the substance is dissolved hot in 25 ml water/5 ml glacial acetic acid. After cooling, it is filtrated and the filtrate is neutralized with ammonia. The pure amimomethyl compound separates out, it is isolated by means of suction and washed with water and isopropanol.

Yield: 6.2 g (66.2 percent of theoretical)

Step 3

2-acetamidomethyl-4-nitro-phenol 2 g (0.012 mole) of the aminomethyl compound from step 2 is dissolved in 20 ml glacial acetic acid and stirred overnight at room temperature with 10 ml (10.87 g=0.11 mole) acetic anhydride.

Next, the glacial acetic acid and the excess acetic anhydride is distilled off in a vacuum, and the residue is recrystallized from butanol. The monoacetyl compound is obtained in the form of yellowish crystals having a melting point of 187° C.

Yield: 2.3 g (90.4 percent of theoretical)

Elemental Analysis:

|     | calculated | found |
| --- | --- | --- |
| % C | 51.42 | 51.90 |
| % H | 4.79 | 4.84 |

NMR Spectrum: 11.26 (s, broad, OH, the signal disappears when agitating the sample with $D_2O$), 8.42 (t, broad, J=6 Hz, NH, the signal disappears when agitating the sample with $D_2O$), 8.09 and 8.02 (signal doesn't disappear, 3-H and 5-H), 6.99 (d, J=10 Hz, 6-H), 4.24 (d, J=6 Hz, benzyl-$CH_2$, the coupling disappears when agitating the sample with $D_2O$), 1.92 (s,

$CCH_3$).

IR Spectrum: (KBr pellet) 646, 762, 848, 918, 1021, 1055, 1093, 1145, 1248, 1298, (broad), 1345, 1495, 1540 (shoulder), 1590 (broad), 1630 (shoulder), 2000 to 3500 (broad, sharp band at 3380) nm.

Step 4

2-acetamidomethyl-4-amino-phenol 2.3 g (0.012 mole) of the nitro compound of step 3 is dissolved in ethanol and hydrated with hydrogen using a platinum catalyst. After absorbing the theoretical quantity of hydrogen the catalyst is suction filtered off, acidified with hydrochloric acid, and the solvent is evaporated in a vacuum. The compound forms a non-crystallizing oil.

Yield: 1.8 g (90.3 percent of theoretical)

Example 2

N-(5-amino-2-hydroxy-benzyl)-N',N'-diethyl-ethylenediamine (Method C)

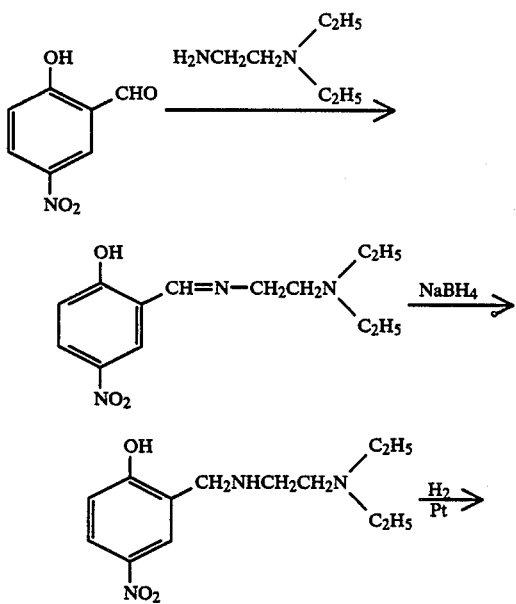

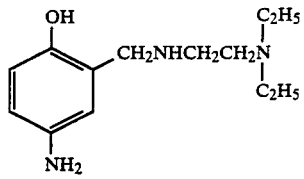

Step 1

N-(2-hydroxy-5-nitro-benzylidene)-N',N'-ethyl-ethylenediamine 16.7 g (0.1 mole) 2-hydroxy-5-nitro-benzaldehyde is boiled in 100 ml absolute methanol with 20 g (0.17 mole) N,N-diethyl-ethylenediamine for 2 hours accompanied by refluxing. When cooling, the Schiff's base crystallizes out. The melting point is 116° to 117° C. The compound is used without further purification in step 2.

Yield: 17.8 g (67 percent of theoretical)

Step 2

N-(2-hydroxy-5-nitro-benzyl)-N',N'-diethyl-ethylenediamine 17.3 g (0,065 mole) benzylidene compound of step 1 is dissolved in 100 ml methanol and added by small amounts with a total of 3 g (0.079 mole) sodium borohydride at room temperature accompanied by stirring. After 1 hour, the solvent is evaporated in a vacuum, the residue is acidified with concentrated hydrochloric acid and evaporated again to dryness. After adding acetone, the hydrochloride is isolated by means of suction and is recrystallized from ethanol. By means of adding ammonia, the free base is produced, this can be purified by means of recrystallization from ethylacetate.

Melting point: 72° C.

Yield: 8.5 g (49 percent of theoretical)

NMR Spectrum: 8.01 (d, J=3 Hz, 6'-H), 7.90 (dd, $J_1$=3 Hz, $J_2$=9 Hz, 4'-H), 6.82 (s, broad, OH, NH; the signal disappears when agitating the sample with $D_2O$), 6.37 (d, J=9 Hz, 3'-H), 3.97 (s, benzyl-$CH_2$), 2.9 to 2.45 (m, —N—$CH_2$—), 0.98 (t, J=7 Hz, $CH_2C\underline{H}_3$).

Step 3

N-(5-amino-2-hydroxy-benzyl)-N',N'-diethyl-ethylenediamine 8.5 g (0.032 mole) of the nitro compound of step 2 is hydrated with hydrogen using a platinum catalyst in a manner analogous to example 1, step 4. After the processing, the very hygroscopic dihydrochloride is obtained.

Yield: 4.9 g (65 percent of theoretical)

NMR Spectrum: 11.4 to 8.5 (broad, NH, OH; the signals disappear when agitating the sample with $D_2O$), 7.46 (s, 6'-H, signal widened by means of coupling with 4-H), 7.32 and 7.12 (d, J=9 Hz, 3'-H and 4'-H, signals widened in each case). 4.3 to 3.0 (m, —N—$CH_2$—), 1.25 (t, J=7 Hz, $CH_2$—$C\underline{H}_3$).

Example 3

N-(5'-amino-2'-hydroxybenzyl)-oxazolidin-2-one

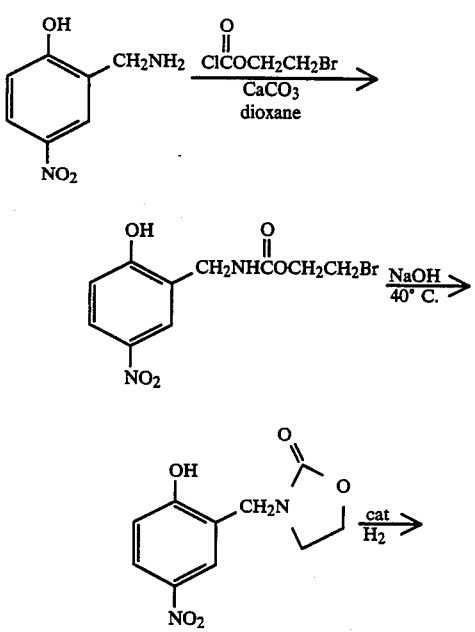

Step 1

N-(2'-hydroxy-5'-nitrobenzyl)-carbamic acid-2-bromoethane ester 16.8 g 2-aminomethyl-4-nitrophenol (example 1, step 2) is suspended in 100 ml dioxane with 8 g calcium carbonate and heated to 95° C. 20 g chloroformic acid bromoethane ester is added by drops, accompanied by stirring, and is then heated another 2 hours to the same temperature. It is poured on ice water, decomposed with concentrated hydrochloric acid of excess calcium carbonate and suctioned from the separated urethane, accompanied by rewashing with water.

Bright yellow crystals are obtained with a melting point of 128° C.

Step 2

N-(2'-hydroxy-5'-nitrobenzyl)-oxazolidin-2-one 6 g of the urethane from step 1 is heated for 1 hour in 270 ml 1% sodium hydroxide solution to 40° C. When acidified with acetic acid the oxazolidinone precipitates out. After recrystallization from n-butanol the compound melts at 228° C.

IR Spectrum (KBr pellet): 752, 825, 1035, 1208, 1280, 1348, 1495, 1595, 1705 (strong), 3200 (broad) nm.

Step 3

N-(5'-amino-2'-hydroxybenzyl)-oxazolidin-2-one

Reduction of the nitro compound of step 2, in a manner analogous to example 2, step 2, results in the amino compound as free base with a melting point of 165° C.

EXAMPLES FOR HAIR DYE COMPOSITION

Example 4

Hair dye composition in gel form

| | |
|---|---|
| 0.50 g | 4-amino-2-aminomethyl-phenol |
| 1.00 g | 2-amino-4-[(2'-hydroxyethyl)-amino]-anisolsulfate |
| 0.15 g | sodiumsulfite, anhydrous |
| 5.00 g | lauryl alcohol-diglycolethersulfate-sodium salt (28 percent aqueous solution) |
| 1.00 g | hydroxyethyl cellulose (highly viscous) |
| 10.00 g | ammonia (22 percent aqueous solution) |
| 82.35 g | water |
| 100.00 g | |

50 g of the hair dye composition described above is mixed with 50 g hydrogen peroxide solution (6 percent) shortly before use, and the mixture is then applied to blond natural hair. After letting it act for a period of 30 minutes at 40° C., the hair is rinsed with water and dried. The hair has an intensive, lustrous red coloring with a light violet cast.

Example 5

Hair dye composition in gel form

| | |
|---|---|
| 0.35 g | 4-amino-2-[(2'-hydroxyethyl)-aminomethyl]-phenol |
| 0.27 g | 5-amino-2-methyl-phenol |
| 0.30 g | ascorbic acid |
| 15.00 g | oleic acid |
| 7.00 g | isopropanol |
| 10.00 g | ammonia (22 percent aqueous solution) |
| 67.08 g | water |
| 100.00 g | |

Shortly before use, 50 g of this hair dye composition is mixed with 50 g hydrogen peroxide solution (6 percent) and the mixture is allowed to act on white human hair for 30 minutes at 40° C. It is then rinsed with water and dried. The hair is dyed an orange shade.

Example 6

Hair dye composition in cream form

| | |
|---|---|
| 1.00 g | 4-amino-2-[bis-(2'-hydroxyethyl)-aminomethyl]-phenol |
| 1.10 g | 1-naphthol |
| 15.00 g | cetyl alcohol |
| 0.30 g | sodium sulfite, anhydrous |
| 3.50 g | lauryl alcohol-diglycolethersulfate-sodium salt (28 percent aqueous solution) |
| 3.00 g | ammonia (22 percent aqueous solution) |
| 76.10 g | water |
| 100.00 g | |

50 g of this hair dye composition is mixed with 50 g hydrogen peroxide solution (6 percent) shortly before using. The mixture is then applied to natural blond hair and allowed to act for 30 minutes at 40° C. It is then rinsed with water and dried. The hair has obtained an intensive red coloring.

Example 7

Hair dye solution

| 0.80 g | 4-amino-2-dimethylaminomethyl-phenol |
| 0.12 g | resorcin |
| 0.10 g | m-aminophenol |
| 0.50 g | 5-amino-2-methyl-phenol |
| 0.10 g | 2,4-diamino-anisolsulfate |
| 0.05 g | 1-naphthol |
| 10.00 g | lauryl alcohol-diglycolethersulfate-sodium salt (28 percent aqueous solution) |
| 10.00 g | ammonia (22 percent aqueous solution) |
| 78.33 g | water |
| 100.00 g | |

50 g of the hair dye composition described above is mixed with 50 g hydrogen peroxide solution (6 percent) shortly before using, and the mixture is allowed to act for 30 minutes at 40° C. on blond natural hair. The hair is then rinsed with water and dried. The hair is colored a fashionable gold-orange shade.

Example 8

Coloring composition in gel form

| 0.90 g | 4-amino-2-aminomethyl-phenol |
| 0.80 g | 2,5-diamino-toluosulfate |
| 0.15 g | 2,4-diamino-anisolsulfate |
| 0.20 g | 5-amino-2-methyl-phenol |
| 0.02 g | 1-[(2'-ureidoethyl)-amino]-4-nitro-benzene |
| 0.05 g | 2-nitro-p-phenylenediamine |
| 0.15 g | sodium sulfite, anhydrous |
| 2.50 g | lauryl alcohol-dyglycolethersulfate-sodium salt (28 percent aqueous solution) |
| 0.80 g | hydroxyethyl cellulose, highly viscous |
| 6.00 g | ammonia, (22 percent aqueous solution) |
| 88.43 g | water |
| 100.00 g | |

50 g of the hair dye composition described above is mixed with 50 g hydrogen peroxide solution (6 percent) shortly before using. The mixture is then applied to blond natural hair. After letting it act for a period of 30 minutes at 40° C., the hair is rinsed with water and dried. The hair has obtained a fashionable brown coloring.

All of the percentages given in the present application are percent by weight.

We claim:

1. A hair dyeing composition comprising a combination of
(A) at least one organic coupler substance customary in hair coloring with the coupler containing a moiety from the group consisting of hydroxy, ether, amino and mixtures thereof; and
(B) a developer substance selected from the group consisting of 4-amino-2-amino-2-aminomethyl-phenol of the formula (I)

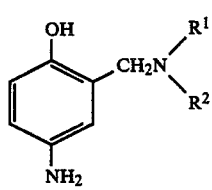

and its physiologically compatible salts with inorganic or organic acids, wherein $R^1$ and $R^2$ independently of one another represent hydrogen, alkyl, hydroxyalkyl, aminoalkyl, mono- or dialkylaminoalkyl, acylaminoalkyl, aryl- or alkylsulfonylaminoalkyl, carbamidoalkyl, alkylsulfonyl, the alkyl radical in each case having 1 to 4 carbon atoms, arylsulfonyl, acyl or carbamoyl, or a heterocyclic, non-aromatic five-membered or six-membered ring, which can have an oxo group in addition, is formed by means of $R^1$ and $R^2$.

2. Composition according to claim 1, characterized in that the developer substance of the formula (I) is selected from the group consisting of 4-amino-2-aminomethyl-phenol, 4-amino-2-[(2'-hydroxyethyl)-aminomethyl]-phenol and 4-amino-2-dimethylaminomethyl-phenol.

3. Composition according to claim 1, characterized in that the coupler substance is selected from the group consisting of 1-naphthol, resorcinol, 4-chloro-resorcinol, 4,6-dichloro-resorcinol, 2-methyl-resorcinol, 2-amino-4-[(2'-hydroxyethyl)-amino]-anisol, 5-amino-2-methyl-phenol, 2,4-diamino-phenoxy-ethanol, 4-amino-2-hydroxy-phenoxy-ethanol, m-aminophenol, 3-amino-2-methyl-phenol, 4-hydroxy-1,2-methylenedioxy-benzene, 4-amino-1,2-methylenedioxy-benzene, 4-[(2'-hydroxyethylamino)]-1,2-methylenedioxy-benzene, 2,4-diamino-anisol, 2,4-diamino-phenetole, 2,4-diaminobenzyl alcohol, m-phenylene-diamine, m-toluylenediamine, 2,4-diamino-phenylethyl alcohol, 4-hydroxyindole, 3-amino-5-hydroxy-2,6-dimethoxy-pyridine and 3,5-diamino-2,6-dimethoxy-pyridine.

4. Composition according to claim 1, characterized in that the developer subtance of the formula (I) is contained in a quantity of 0.01 to 3.0 percent by weight.

5. Composition according to claim 1, characterized in that the total quantity of the developer substance-coupler substance combination amounts to 0.1 to 5.0 percent by weight.

6. Composition according to claim 1, characterized in that it contains a dye component which is selected from the group consisting of 6-amino-2-methyl-phenol, 2-amino-5-methyl-phenol, Diamond Fuchsine (C.I. 42 510), Leather Ruby HF (C.I. 42 520), 2-nitro-1,4-diamino-benzene, 2-amino-4-nitro-phenol, 2-amino-5-nitro-phenol, 2-amino-4,6-dinitro-phenol, 2-amino-5-[(2'-hydroxyethyl)-amino]-nitrobenzene, 2-methylamino-5-[bis-(2'-hydroxyethyl)-amino]-nitrobenzene, Acid Brown 4 (C.I. 14 805), 1,4-diaminoanthraquinone and 1,4,5,8-tetraaminoanthraquinone.

7. Composition according to claim 1, characterized in that it contains ascorbic acid, thioglycolic acid or sodium sulfite as antioxidants.

8. Composition according to claim 1, characterized in that it has a pH value between 8.0 and 11.5.

9. 4-amino-2-aminomethyl-phenol of the general formula (XII)

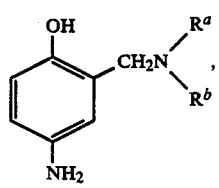

wherein $R^a$ equals hydrogen, alkyl, hydroxyalkyl, aminoalkyl, mono- or dialkylaminoalkyl, acylaminoalkyl, aryl- or alkylsulfonylaminoalkyl, carbamoyl, carbamidoalkyl, acyl, aryl- or alkylsulfonyl—wherein the alkyl radicals have 1 to 4 carbon atoms in each case— —and $R^b$ equals aminoalkyl, mono- or dialkylaminoalkyl, acylaminoalkyl, aryl- or alkylsulfonylaminoalkyl, carbamoyl, carbamidoalkyl, acyl, aryl- or alkylsulfonyl—wherein the alkyl radicals have 1 to 4 carbon atoms in each case.

10. 2-acetamidomethyl-4-amino-phenol.

11. N-(5-amino-2-hydroxy-benzene)-N',N'-diethyl-ethylenediamine.

12. Composition according to claim 2, characterized in that the coupler substance is selected from the group consisting of 1-naphthol, resorcinol, 4-chloro-resorcinol, 4,6-dichloro-resorcinol, 2-methyl-resorcinol, 2-amino-4-[(2'-hydroxyethyl)-amino]-anisol, 5-amino-2-methyl-phenol, 2,4-diamino-phenoxyethanol, 4-amino-2-hydroxy-phenoxy-ethanol, m-aminophenol, 3-amino-2-methyl-phenol, 4-hydroxy-1,2-methylenedioxy-benzene, 4-amino-1,2-methylenedioxy-benzene, 4-[(2'-hydroxyethyl-amino)]-1,2-methylenedioxy-benzene, 2,4-diamino-anisol, 2,4-diamino-phenetole, 2,4-diamino-benzyl alcohol, m-phenylenediamine, m-toluylenediamine, 2,4-diamino-phenylethyl alcohol, 4-hydroxy-indole, 3-amino-5-hydroxy-2,6-dimethoxy-pyridine and 3,5-diamino-2,6-dimethoxy-pyridine.

* * * * *